(12) United States Patent  
Mavliev et al.

(10) Patent No.: US 6,392,745 B1  
(45) Date of Patent: May 21, 2002

(54) METHOD AND APPARATUS FOR THE FAST DETECTION OF SURFACE CHARACTERISTICS

(75) Inventors: Rashid Mavliev, Chicago; Hwa-Chi Wang, Naperville, both of IL (US)

(73) Assignee: American Air Liquide, Inc., Fremont, CA (US)

( * ) Notice: Subject to any disclaimer, the term of this patent is extended or adjusted under 35 U.S.C. 154(b) by 0 days.

(21) Appl. No.: 09/593,644

(22) Filed: Jun. 13, 2000

(51) Int. Cl.[7] .................. G01N 1/00; G01N 21/00
(52) U.S. Cl. ........................ 356/37; 356/237.3
(58) Field of Search .................. 356/36, 37, 38, 356/237.1, 237.2, 237.3, 237.4, 237.5, 381, 382, 495, 239.1, 239.2, 239.3, 239.7, 239.8, 335–337, 338; 250/574, 559.4, 559.41; 382/141, 144, 145; 414/217

(56) References Cited

U.S. PATENT DOCUMENTS

| | | | | |
|---|---|---|---|---|
| 5,444,529 A | * | 8/1995 | Tateiwa | 356/337 |
| 5,640,237 A | * | 6/1997 | Esrig et al. | 356/237 |
| 5,909,276 A | * | 6/1999 | Kinney et al. | 356/237 |
| 5,940,175 A | * | 8/1999 | Sun | 356/237.3 |
| 5,971,609 A | * | 10/1999 | Kijima et al. | 374/17 |
| 6,025,601 A | * | 2/2000 | Trulson et al. | 250/461.2 |
| 6,136,096 A | * | 10/2000 | Morishige | 118/720 |

* cited by examiner

Primary Examiner—Frank G. Font  
Assistant Examiner—Michael P. Stafira  
(74) Attorney, Agent, or Firm—Linda K. Russell

(57) ABSTRACT

A method and apparatus for quickly detecting the surface characteristics of a surface, such as features, anomalies or contaminants are disclosed. The method and apparatus use heterogeneous condensation of a vapor on a surface and evaporation to reveal the surface characteristics of the surface and thereby enable the detection of such features.

27 Claims, 18 Drawing Sheets

METHOD AND APPARATUS FOR THE FAST DETECTION OF SURFACE CHARACTERISTICS

BACKGROUND OF THE INVENTION

1. Field of the Invention

The present invention relates to the optical detection of the characteristics or features of a surface, including but not limited to anomalies or contaminants which can be found on such surface. Furthermore, the present invention relates to the method and apparatus which detects light reflected or scattered from the entire surface subject to heterogeneous condensation of a vapor and evaporation in order to reveal the surface characteristics of the surface without destroying the surface itself.

2. Description of the Art

The inspection of the surface features of a wafer is a critical step in the manufacturing process of microelectronic devices because contamination is a source of loss of yield during the manufacturing process. Typically, wafers are inspected repeatedly during the manufacturing process. As the size of the device features shrinks, the detection of such features as well as anomalies on the wafers themselves becomes increasingly difficult using conventional optical methods. In addition, these conventional methods are generally slow since many times only a portion of the wafer is scanned.

Optical instruments have long been used to detect, locate and size particles on semiconductor wafers. Generally, the practical detection limit of particles on bare silicon wafers is about 0.1 to 0.2 micrometers. Since the amount of scattered light from a particle is proportional to $d^6$, where d is the particle diameter, a reduction in particle size by a factor of 2 results in a 64-fold decrease in scattered light. As a detection rate of about one to three wafers per minute is generally desired, and the number of photons scattered from a light source falls into the range of about 0.1 micrometers, detection becomes very difficult with conventional devices. Even at these small sizes, anomalies or contaminants can be detrimental to the surface and even the entire device itself. Once a contaminant, defect, anomaly or uncharacteristic feature is found, the entire batch of wafers may have to be reworked or disposed of.

U.S. Pat. No. 3,580,066 to Pliskin describes a method of determining the completeness of oxide etching of via holes in a silicon member surface, in which the silicon member is cooled while a stream of moist gas is directed onto its surface. The stream of moist gas is produced by bubbling dry nitrogen through de-ionized water. Condensation in the holes is in the form of a thin film over residual oxide but beads into droplets over bare silicon.

U.S. Pat. No. 4,314,474 to Dermarderosian describes a method in which an inert fluorocarbon vapor is condensed on a test surface in order to detect cracks, fissures and other such faults on the surface. A liquid fluorocarbon contained in a flask is heated to a gentle boil while an inert gas, such as air or nitrogen, is bubbled through the liquid. A mild flow of vapor is carried from the flask to the test surface by a vapor tube, the free end of which is held from about ½ inch to 1 inch (approx. 2 cm) away from the test surface. The fluorocarbon has a surface tension sufficiently low that as it condenses it wets the surface, forming a layer of uniform thickness. Detection is visual and may be made with the aid of a microscope and relies on the fact that faulted regions absorb comparatively more of the incident light than unfaulted regions. Defects on the order of one micrometer in size are visible.

U.S. Pat. No. 4,967,095 discloses a method and apparatus for detecting and classifying particles on a surface using condensation. The apparatus includes a heatable wick disposed over a test surface and in fluid communication with a source of volatile liquid. A zone of vapor supersaturation is created on the surface in which condensation on the particles of the surface can occur. A light beam is directed onto the surface. The droplets are detected by means of light scattered from the droplets.

U.S. Pat. No. 5,608,155 to Ye et al., discloses a method to enlarge the apparent size of sub-micron contaminant particles on a substrate by selective condensation of a vapor on the substrate. The substrate is apparently located proximate to and spaced apart from a liquid vapor source that is heated. The vaporized liquid apparently adheres to the particles and according to the patentee, after a predetermined period of time, condensation of the vapor on the substrate is stopped. The substrate is scanned for detecting the particles.

A need still exists for a simple apparatus and method to determine the surface characteristics or features of an entire surface which is nondestructive and which can quickly show the surface characteristics.

DESCRIPTION OF PREFERRED EMBODIMENT

Figure 1:
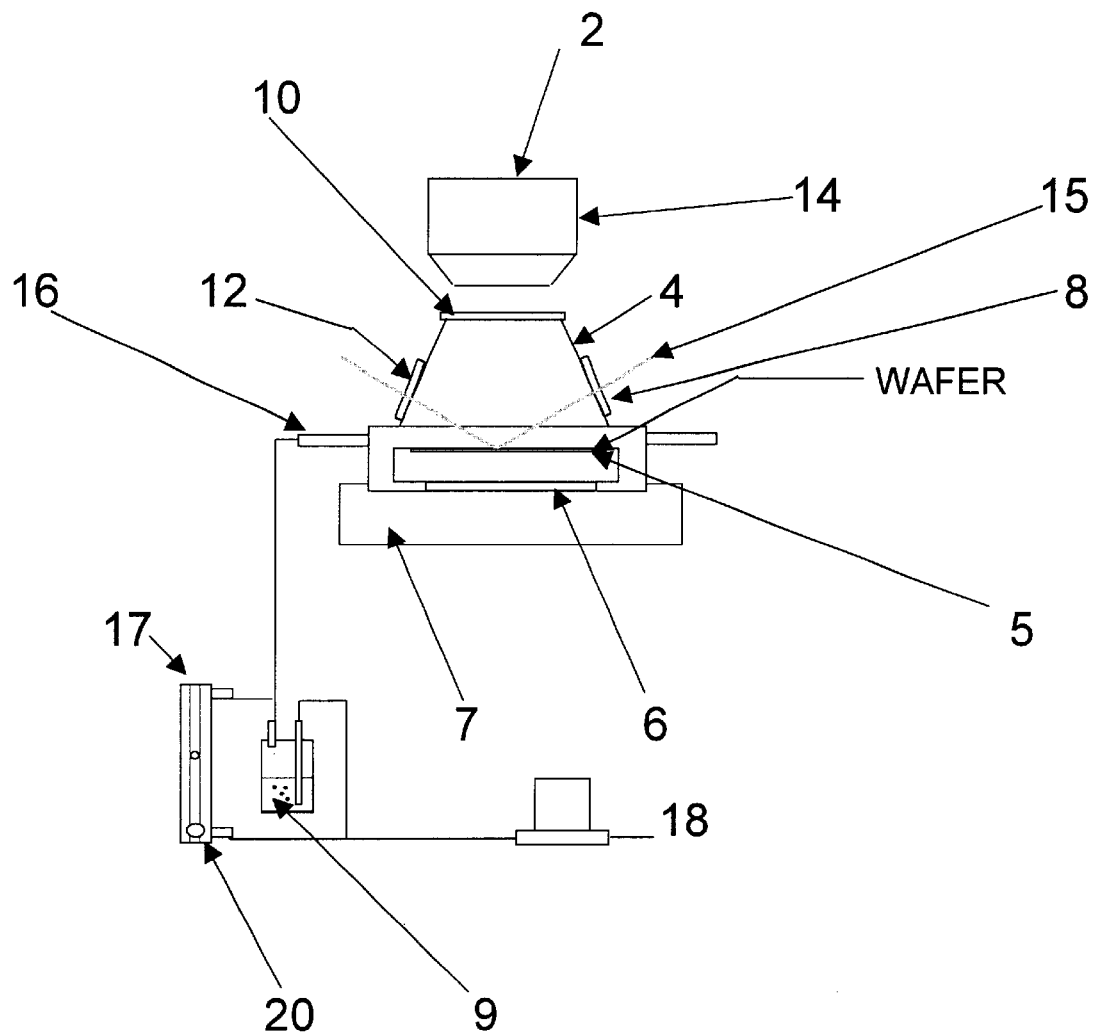
FIG. 1 is a schematic of possible embodiment of the apparatus according to an aspect of the invention.

The present invention uses heterogeneous condensation of a vapor on a surface to determine the surface characteristics or features of the surface itself. By the present invention, vapor is delivered to the surface whose surface characteristics or features are to be determined. The vapor condenses and by the process of heterogeneous nucleation produces a high concentration of droplets on the surface. The size, distribution and concentration of the droplets nucleated on the surface depend strongly upon the interfacial surface tension which is a function of surface properties of the surface itself. During condensation of the vapor, as well as during evaporation of the vapor, when the surface is illuminated, the light is scattered and reflected by the droplets. Preferably, the entire surface of the sample being tested is covered with the condensate prior to illumination. This scattered and reflected light can be detected by an optical detector. Therefore, minute variations in the surface can be seen. This test is quick, easy and nondestructive. Furthermore, the test can itself be incorporated into the manufacturing process line to provide quick and reliable information about the surfaces being manufactured.

The apparatus and the method of the invention utilize the concepts of supersaturation in conjunction with condensation and evaporation to operate. If the vapor pressure of the carrier gas is equal to the equilibrium vapor pressure at a given temperature, then the gas stream is saturated with the fluid vapor. If the vapor pressure can be made to exceed its equilibrium vapor pressure, then the carrier gas is called supersaturated. Supersaturation is a non-equilibrium condition and the carrier gas will attempt to return to equilibrium by condensing some of the vapor out onto either a surface or a particle present in the gas stream. The process of condensation of vapor onto surface is always accompanied with evaporation process. In case of condensation of vapor on particle surface the relationship between vapor pressure and particle diameter when the process of condensation starts to prevail over evaporation (Kelvin diameter) is $$d_{kelv} = \frac{4\sigma M}{\rho RT \ln S}, \tag{1}$$

where $d_{kelv}$ is the Kelvin diameter, σ is surface tension, M is molecular weight, p is density of liquid, R is the universal gas constant, and the supersaturation $S=P/P_{sat}$ (T). At a given S value, particles greater than the Kelvin diameter are activated and followed by condensational growth. Particles smaller than the Kelvin diameter are not activated and eventually evaporate.

In case of condensation of the vapor on substrate, the critical nucleus may be considered as a spherical cap surrounded by metastable gas or vapor. It is assumed that cluster grows with constant wetting angle θ, which can be determined from Young's equation $$\cos\theta = \frac{\sigma_{gs} - \sigma_{ls}}{\sigma_{gl}} \tag{2}$$

where $\sigma_{ij}$ is surface tension of i-j interface, subscripts l, g and s denoting, respectively, liquid, gas and substrate. The cluster free energy can be written in the usual form for homogeneous free energy $G_{hom}$ (which is function of gas and liquid properties only and does not include any properties of substrate) multiplied by volume fraction v(θ) of liquid cap (see FIG. 1), where v(θ) is $$v(\theta) = \frac{(2+\cos\theta)(1-\cos\theta)^2}{4} \tag{3}$$

Under the classical nucleation theory, the rate of formation of critical droplets per unit area $J_{cl}$ is expressed in the following manner $$J_{cl} = J_0 \exp\left(-\frac{G_{het}}{kT}\right) \tag{4}$$

where $J_0$ is pre-exponential factor, which depends on the assumed mechanism for particle deposition, and $G_{het}= G_{hom}*v(\theta)$. Although there are various other mechanisms that exist to explain the particle deposition, even this simplified approach shows strong dependence of $J_{cl}$ on surface tension and specifically on (θ). Estimates (Wu, 1997, p. 56) show that variation of (θ) in the range of 60–120° can vary the rate of particle formation per unit area in 25 orders of magnitude. Therefore, the process of condensation of the vapor particles on a cold surface from metastable gas/vapor media has an extreme sensitivity to surface properties and should be useful in the diagnosis of both surface properties and anomalies. These concepts are used in the apparatus and the method of the instant invention. With the concepts, one is able to shine light on a surface upon which a vapor has condensed and to detect the surface characteristics of the surface during the condensation process as well as during evaporation of the vapor from the surface.

Figure 2:
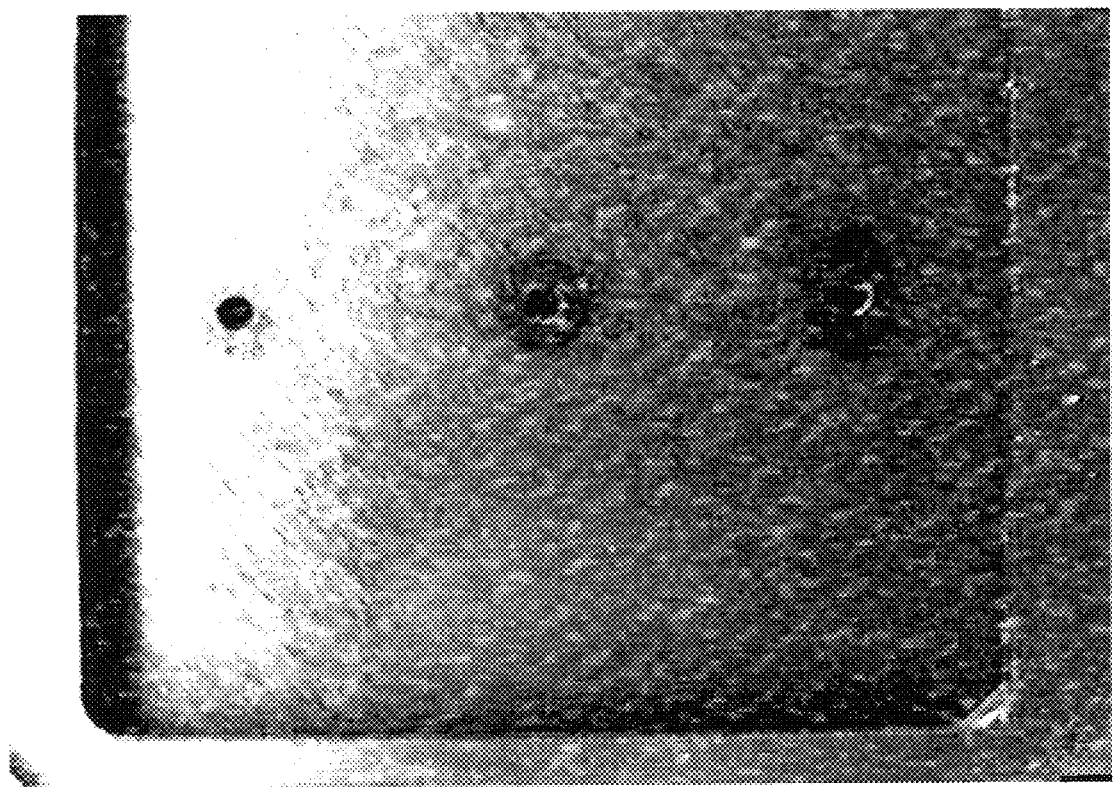
FIG. 2 is a photograph of the cooling device that can be used in the apparatus of FIG. 1, if desired.

Referring now to FIG. 1, an exemplary embodiment of an apparatus 2 incorporating the above concept and method is presented according to an aspect of the invention. The apparatus 2 comprises a test chamber 4 with a holder 5 for the test sample. The test chamber has a cooling device 6. Any type of cooling device can be used in the apparatus provided that the surface of the test surface or substrate can be cooled sufficiently to achieve condensation of any vapor that is introduced over the wafer. That is, the cooling device must maintain the test sample at a temperature on which the vapor phase of the vaporizable material will condense on the surface of the sample and then evaporate. Preferably, a thermoelectric cooling device with a heat sink is used. An example of a thermoelectric device is a thermoelectric cooler, model number Cl.4-127-045L, available from Melcor Corp., Trenton, N.J. Most preferably, a thermoelectric cooling device with a vacuum source to hold the wafer in the device as shown in FIG. 2 is used. In addition, the test chamber 4, includes a heat sink 7 located near the thermoelectric cooling device and the sample holder 7.

The chamber 4 also has a light source as well as an optical detector 14 that is used in conjunction with the light source 15 to detect the light scattered from the condensate droplets after condensation of the vapor on the surface of the sample as being tested as well as during evaporation. Three optical ports or windows 8, 10 and 12 are included on the chamber. Optical window 10 is provided to enable the optical detector to detect the particles after condensation as the light source illuminates the test surface through window 8. Although shown in this manner, the apparatus can have any number of windows or ports so long as the optical detector is able to detect the light scattered and reflected from condensate on the surface of the sample when the surface of the sample is illuminated during condensation and/or evaporation.

Light source 15 can be any light source. Preferably, the light source can be a visible or infrared light source. Desirably, the light source has a wavelength in the range of about 400 to about 800 nanometers. Preferably, the light source 15 is a white light. In the experiments discussed later, a 25-watt fluorescent desk lamp was used. In the embodiment shown, the optical detector 14 is operatively connected to the test chamber via a window or port 10 in order to receive light scattered or reflected by the condensation droplets on the surface due to the condensation of the liquid particles. The optical detector can by any type of optical detector including any photographic camera or television camera provided that the detector can detect the condensate on the surface being tested. Preferably, the optical detector can record the image of scattered or reflected light from the surface in the test chamber. The optical detector should be able to record such images during both condensation of the vapor as well as during evaporation.

In addition, the apparatus of FIG. 1 includes an inlet 16 for introducing a vaporizable material into the chamber, as well as a source for vaporizable material 17. The vaporizable material can be any vaporizable material provided it is compatible with the surface being tested and that is quickly evaporates from the surface. Alternatively, a carrier gas bearing vapor phase particles can be used as the vaporizable material. In such case, the vapor phase particles are deposited into the carrier gas stream by passing the carrier gas 18 stream over a pool of liquid, such as water 19. The carrier gas can be any inert gas, such as for example, but not limited to nitrogen, argon and helium, provided that the carrier gas can hold the vapor particles. A flowmeter 20 or other type of regulator device can be used to regulate the flow of the carrier gas with vapor into an inlet in the test chamber. The test chamber also includes an exit for the vaporizable material. Similarly, although not integral to the apparatus of the instant invention, a flow mass controller may be incorporated into the device, if desired for convenience. The flow mass controller can help further regulate the flow of the carrier gas with vapor into the test chamber.

Any type of sample or substrate on which surface characteristics, features anomalies or contaminants are to be detected can be tested. Examples of surfaces to be tested include optical surfaces and wafers. Preferably, the sample is a wafer used in the manufacture of electronics. Most preferably, the wafer is a silicon wafer. The silicon wafer can be doped with a species such as boron or phosphorus to enhance its electronic properties. Alternatively, other dopants or even other wafers can be used as test samples in the apparatus of the instant invention.

The components and parts of this apparatus as described above can be varied, changed, modified or deleted provided that the apparatus introduces a vaporizable liquid material in vapor form over the test sample, enables the vapor to condense on the sample, and provides a light source and a optical detector to detect the light scattered from the vapor which has condensed on the surface or which is evaporating from the surface.

The invention also comprises a method for detecting the surface features of a sample, without destruction of the sample itself. The method comprises exposing a surface of a sample with a supersaturated vapor, maintaining the surface of the sample cooler than the vapor, condensing the vapor on the test sample, illuminating the test sample with light and detecting the light scattered and reflected from the vapor droplets condensed on the surface features of the test sample. The sample can similarly be illuminated after condensation and during the evaporation in the same manner as described to discern the surface characteristics of the sample surface.

To experimentally verify the present invention, numerous experiments, described below in greater detail were conducted using the apparatus illustrated in FIG. 1. The surfaces to be tested in the experiments conducted herein were wafers. The wafers were bare silicon wafer, SEMI spec. test wafers, single side polished having a two-inch diameter, 10–12 mils. available from Silicon, Inc., Boise, Id. The wafer used in the examples set forth below are described in the following table:

TABLE I

| Wafer No. | Type | Dopant |
|---|---|---|
| 1 | <100> | Boron |
| 2 | <100> | Boron |
| 3 | <111> | Boron |
| 4 | <111> | Boron |
| 5 | <100> | Phosphorus |
| 6 | <100> | Phosphorus |
| 7 | Unknown | Undoped |
| 8 | Unknown | Undoped |

As seen from Table I, some of the wafers were doped with a dopant. The wafers were placed into an apparatus of the instant invention comprising a chamber. The test wafer is placed on a sample holder located in such chamber. The temperature of the wafer is controlled by thermoelectric cooling device located by the sample holder. FIG. 2 shows the holder with the cooling device which was used. Three holes are found in the middle of the holder attached cooling device to enable the test wafers to be held on the device by vacuum, if so desired. Generally, the experiments were conducted at a constant wafer temperature of 8° C.

A carrier gas, dry nitrogen partially saturated with water vapor is introduced to the chamber. The flow rate of the gases used in these experiments was approximately 1 to about 1.5 liters per minute. The saturation level of the carrier gas is controlled by the adjustment of the flow rate of both the carrier gas and the saturated gas.

To begin the experiments, a wafer is placed upon the sample holder in the chamber of the apparatus of the instant invention. During the period of the initial temperature adjustment of the wafer, dry nitrogen is introduced to the chamber at approximately 1 liter per minute. The test sample is cooled to a temperature below the temperature of the gas. The concentration of the water vapor in the nitrogen is slowly increased so as to be able to obtain heterogeneous nucleation of vapor on the wafer. The vapor condenses as it flows over the surface of the sample. As the vapor condenses, a layer of water droplets covers the entire wafer surface. A light is used to illuminate the surface of the wafer. The surface of the wafer with condensate on it from the vaporizable material is illuminated and the illumination is recorded using a photo camera (WAT-902A from The Watec Co., Ltd., in Japan) or a video cam recorder from Hitachi (Model VM-H835LA). The water vapor in the carrier gas is then reduced. The condensate film evaporates from the wafer. The surface of the wafer can also be illuminated during the evaporation of the vapor from the wafer. Surface characteristics can still be detected even during the evaporation process.

The results of the experiments are set forth in the attached Figures which are photographs. The exact size of the frames of the photographs as well as the amplification can be varied. These variations can be carried out simply by one of ordinary skill in the art and have no bearing upon the invention, so long as the variation on the surface can be detected by the illumination of the condensate.

EXAMPLE 1

This example was conducted to illustrate the ability of the apparatus and method of the instant invention to detect polishing marks on the surfaces of the samples themselves. The wafers, numbers 1 and 2 in Table I, were used in this experiment. These wafers were doped with boron and polished by the manufacturer. The wafers were placed on the sample holder in the chamber and subject to treatment according to the method of this invention. The results of the experiment can be seen in FIG. 3 and FIG. 4. The marks distinguishable in the photograph appear to be polishing marks.

EXAMPLE 2

This example illustrates the ability to use the present invention in the detection of the wafer dopant structure itself. Doping of the silicon wafers modifies the surface properties of the wafers themselves and can now be detected with the novel method and apparatus of the instant invention. Two wafers, wafer numbers 5 and 6 of Table I, were used in this example. Both wafers were doped with phosphorus. When tested, each wafer was placed in the holder in the chamber and subject to the method set forth above. The results of the experiments can be seen in FIGS. 5 and 6.

Figure 3:
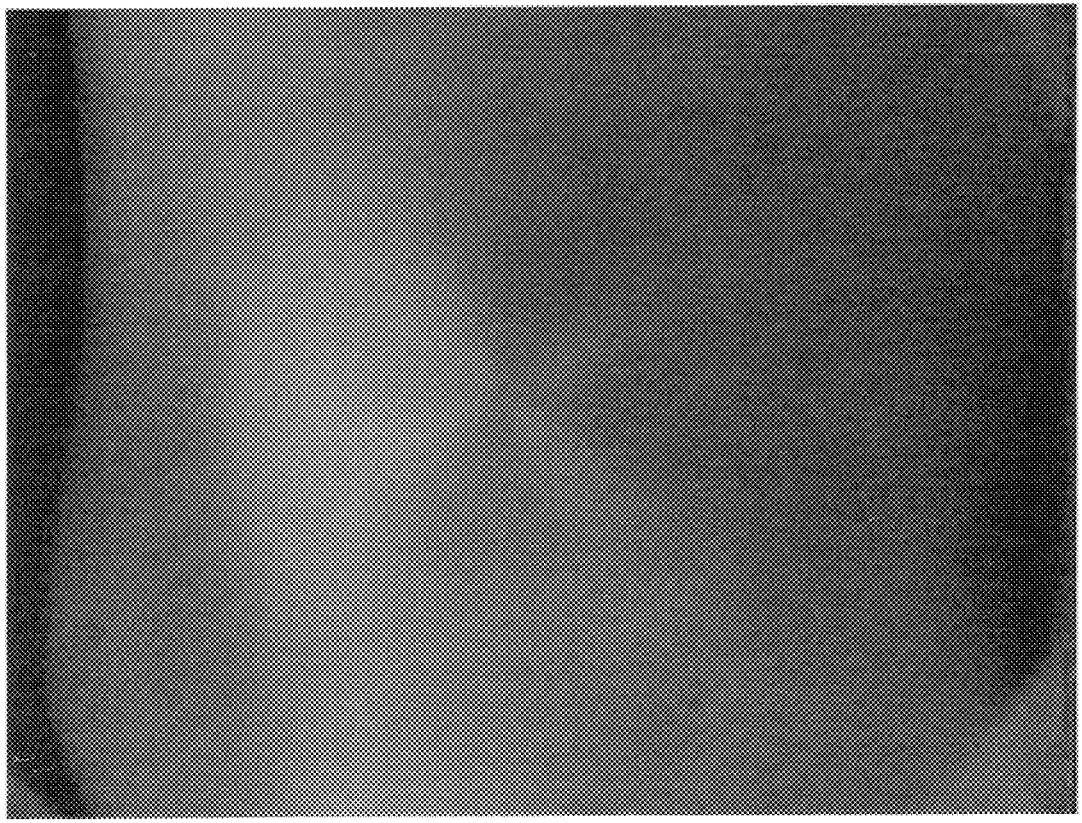
FIG. 3 is a photograph that illustrates the light scattering pattern of the condensate on a typical wafer detected by a camera.
Figure 4:
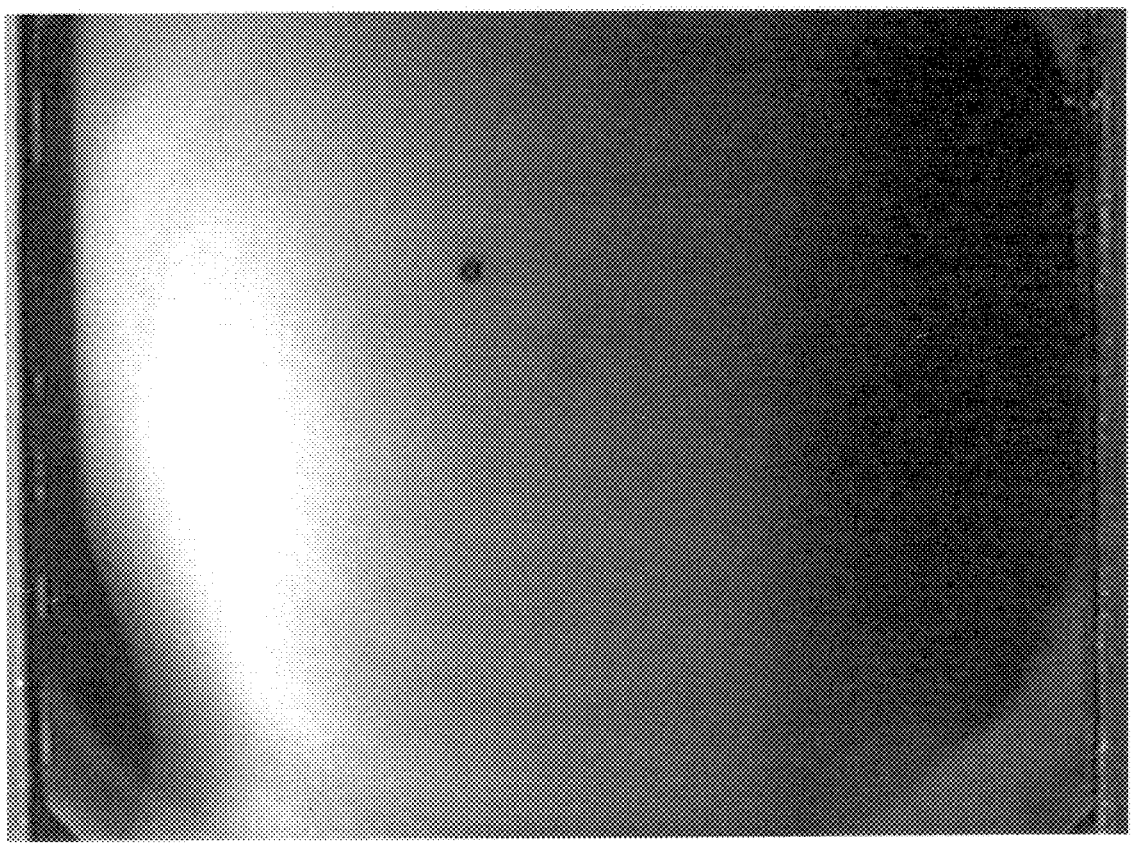
FIG. 4 is a photograph that illustrates the light scattering pattern of the condensate on a wafer prior to partial coverage with a gold film as detected by a camera.
Figure 5:
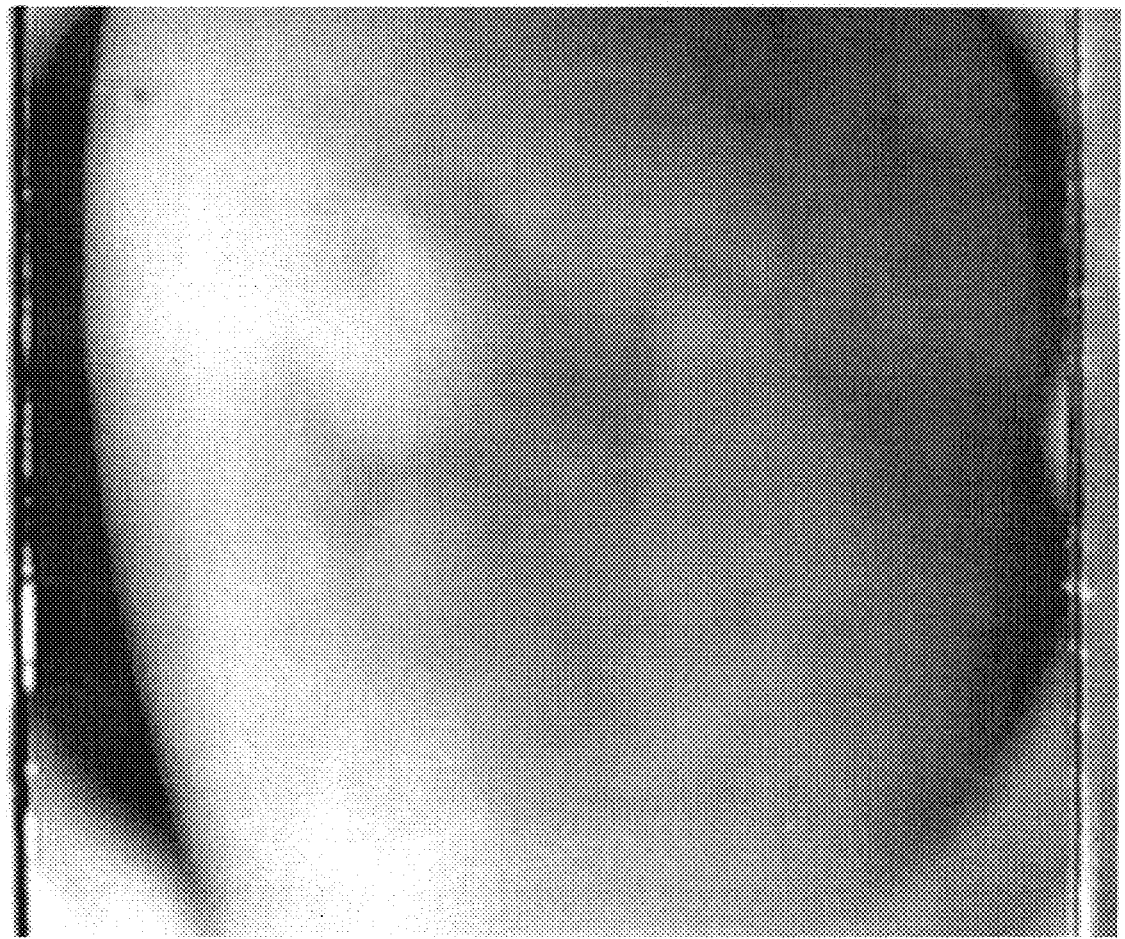
FIG. 5 is a photograph that illustrates the light scattering pattern of the condensate on a wafer having an irregular doping pattern of the wafer itself as detected by a camera.
Figure 6:
FIG. 6 is a photograph that illustrates the light scattering pattern of the condensate on a wafer prior to being contaminated with a drop of water as detected by a camera.

The structure of the condensate shown in FIGS. 5 and 6 is dramatically different from the structure of FIGS. 3 and 4 in which boron doped silicon wafers were used. It is believed that these differences are due to the spatial irregularities of the each of the doping processes as well as the differences in the dopants which leads to a variation in the surface characteristics.

EXAMPLE 3

This example demonstrates the possibility of detecting contaminants on the wafer surface such as water droplet marks. In this example, a silicon wafer doped with phosphorus was used (wafer number 6 of Table I). The initial structure of the condensate from the wafer itself subject to the method of the invention is shown in FIG. 6.

A water droplet is then placed in the center of the wafer on a syringe and is pulled along the surface of the wafer from the center of the wafer to the side of the wafer. Since the wafer surface is hydrophobic, the water droplet remains attached to the syringe the entire time that it is pulled across the surface of the wafer. The wafer is once again subject to the method described above. The condensate structure on the wafer itself after this procedure can be seen in FIG. 7. The water droplet mark is clearly visible on the photograph.

Figure 7:
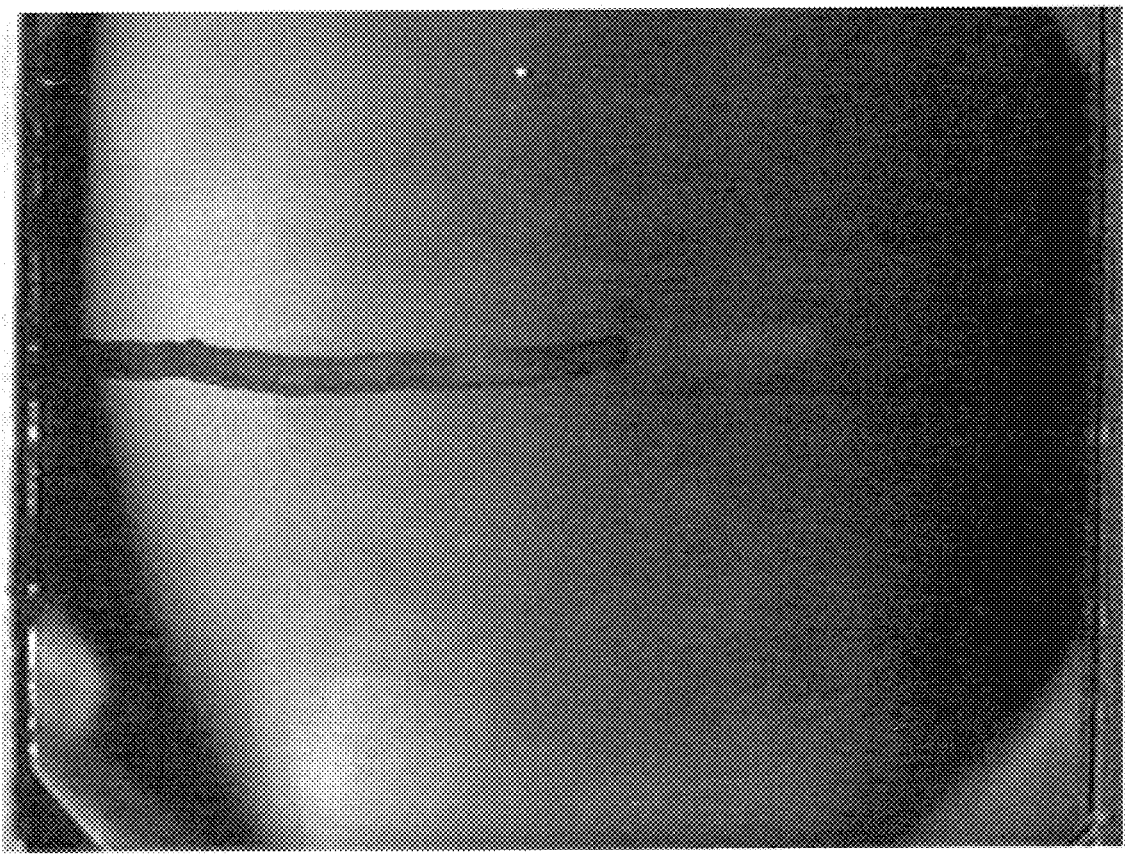
FIG. 7 is a photograph that illustrates the light scattering pattern of the condensate on a wafer after a drop of water was run across the wafer as detected by a camera.

The results of FIGS. 6 and 7 show that as the surface of the wafer is modified, it leads to the change of the surface tension and therefore changes the rate of heterogeneous nucleation of vapor on the wafer surface. The number of particles condensed per unit area and condensate particle size become different for modified surfaces as compared to the unmodified surface. Furthermore, this example also illustrates the sensitivity of the instant invention to the detection of even a drop of water.

EXAMPLE 4

Figure 8:
FIG. 8 is a photograph that illustrates the light scattering pattern of the condensate on a wafer bearing fingerprint marks as detected by a camera.

In this example, the ability of the apparatus and the method to detect contaminants such as fingerprints was studied. In this experiment, fingerprints were placed on a boron-doped wafer (wafer number 4 of Table I) prior to being subject to the method set forth above. FIG. 8 illustrates the structure of the condensate on the surface of the wafer. The fingerprints are easily detectable from the photograph.

Figure 9:
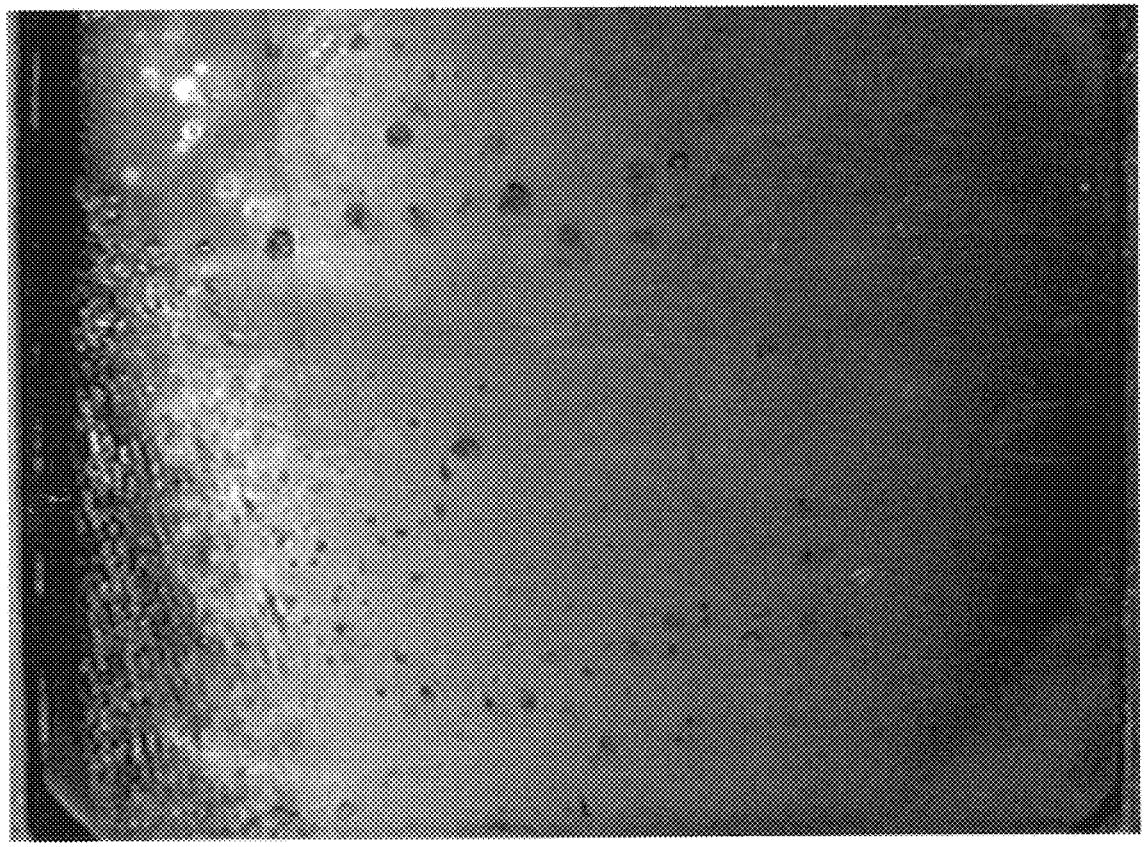
FIG. 9 is a photograph that illustrates the light scattering pattern of the condensate on a dirty wafer contaminated with fingerprint marks, particles and acetone residue as detected by a camera.

Similarly, an undoped dirty wafer was subject to the method of the instant invention. An acetone residue mark was placed on the wafer by pulling an acetone drop from the center of the wafer to the side of the wafer. The results of this particular experiment are illustrated in FIG. 9. It is believed that the marks in the upper right hand corner signify the acetone residue marks. Similarly, it is believed that the marks in the lower right hand corner are due to fingerprint marks on the wafer.

EXAMPLE 5

Figure 10:
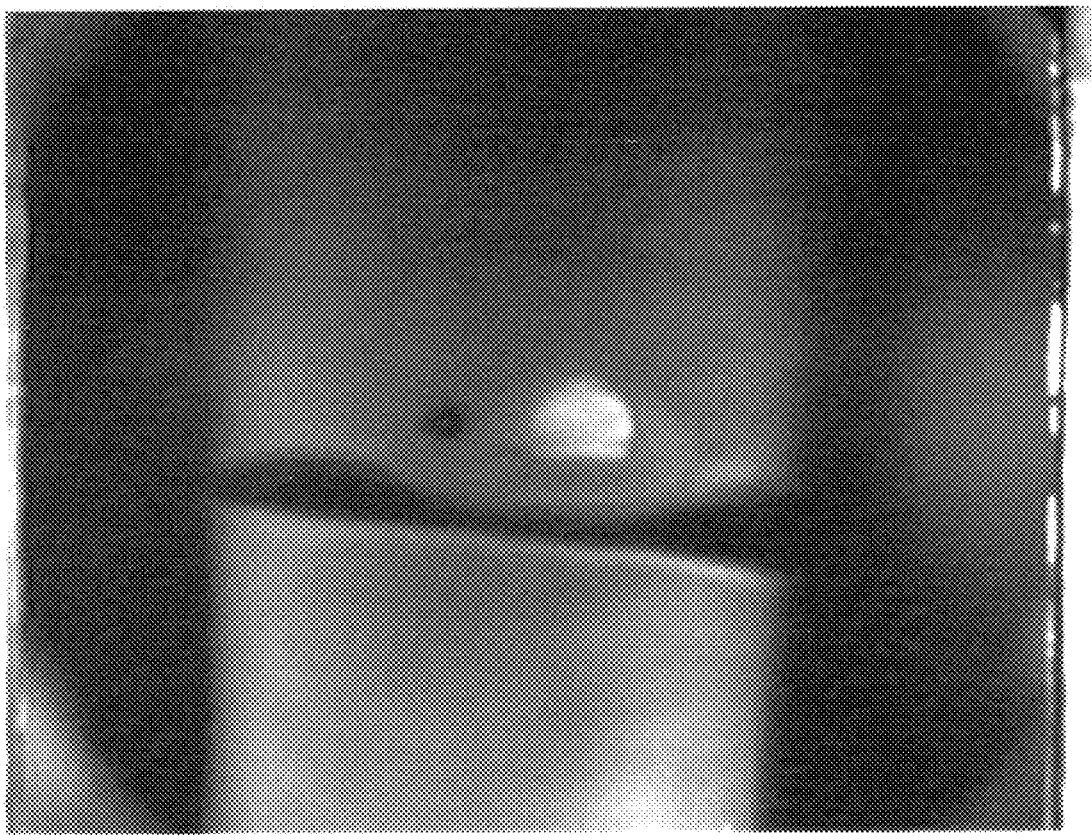
FIG. 10 is a photograph that illustrates the light scattering pattern of the condensate on a wafer of FIG. 5 partially covered with gold as detected by a camera.

This example also demonstrates the possibility of detecting contaminants such as thin films on the wafer surfaces. The wafers used in the experiments were partially covered with a thin gold film. A sputtering device was used to deposit the thin gold film on the wafer surface (wafer number 1 of Table I) which is covered with a copper foil mask having a thin 2 mm. slit. The exposure time for the sputtering device is varied to control the thickness of the film deposited. In the first experiment, a boron doped silicon wafer was exposed for approximately 5 seconds to obtain an estimated film thickness of about 2 nm. The wafer was then subjected to the method of the instant invention. The condensate structure for the wafer can be seen in FIG. 10. The thick line in FIG. 10 shows the area covered by gold. The rounded area in the center of the wafer is believed to be caused by damage to the wafer during the nucleation. In the second experiment, a boron doped silicon wafer (wafer number 3 of Table I) was exposed for approximately 1 second to the sputtering device. The estimated film thickness of the gold in this experiment is about 0.4 nm. The wafer was then subjected to the method. The condensate structure for the wafer can be seen in FIG. 11, once again showing the thick area covered by gold.

Figure 11:
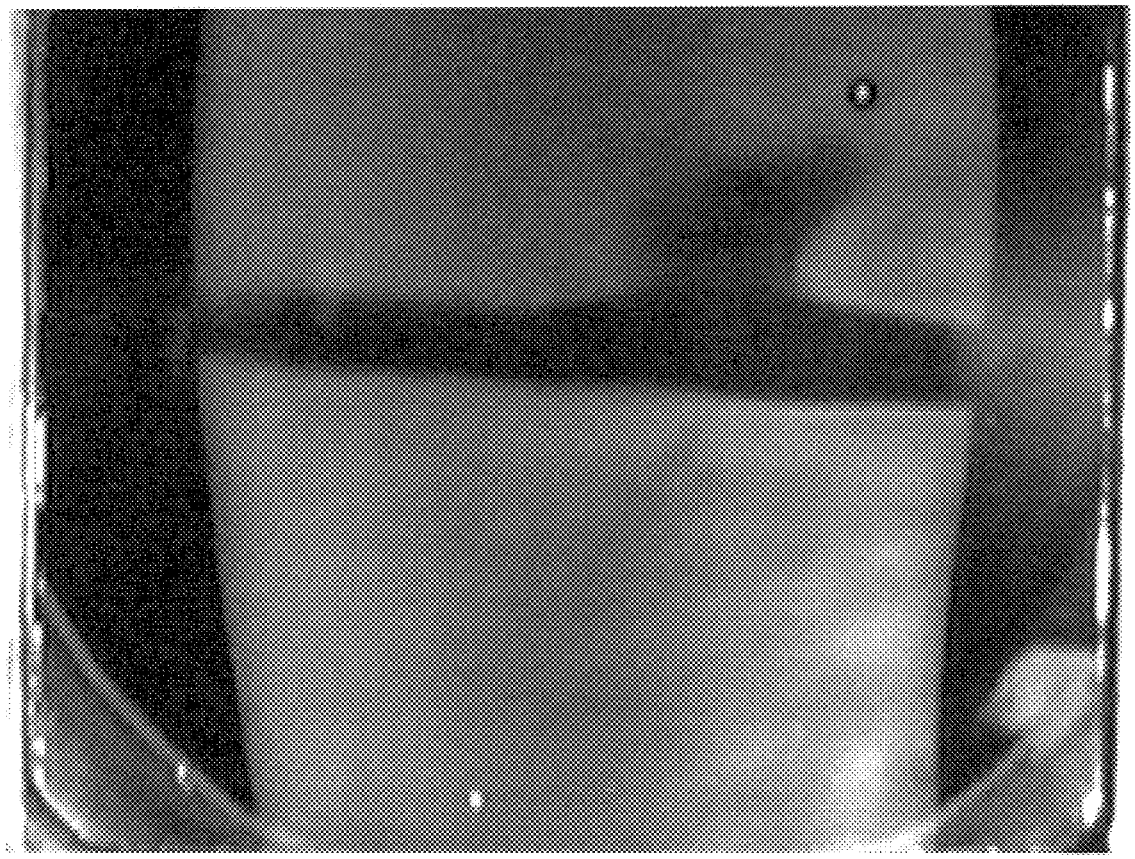
FIG. 11 is a photograph that illustrates the light scattering pattern of the condensate on a wafer after the wafer was partially covered with gold film as detected by a camera.

The results of FIGS. 10 and 11 show that even very thin films on the wafer surface can be detected using the apparatus as well as the method of the instant invention.

EXAMPLE 6

Similarly, this example also shows the possibility of detecting small contaminants on the wafer surface. An undoped wafer (wafer number 7 of Table I) was used in this series of experiments.

Polystyrene latex particles as a wide line in the size range of 50–100 nm were used as the particle contaminants. These particles in a dionized water solution were atomized in a conventional nebulizer and directed to the wafer surface by the nozzle. The wafer was then subjected to the method of this invention. The results of the condensate structure are illustrated in FIG. 12.

Figure 12:
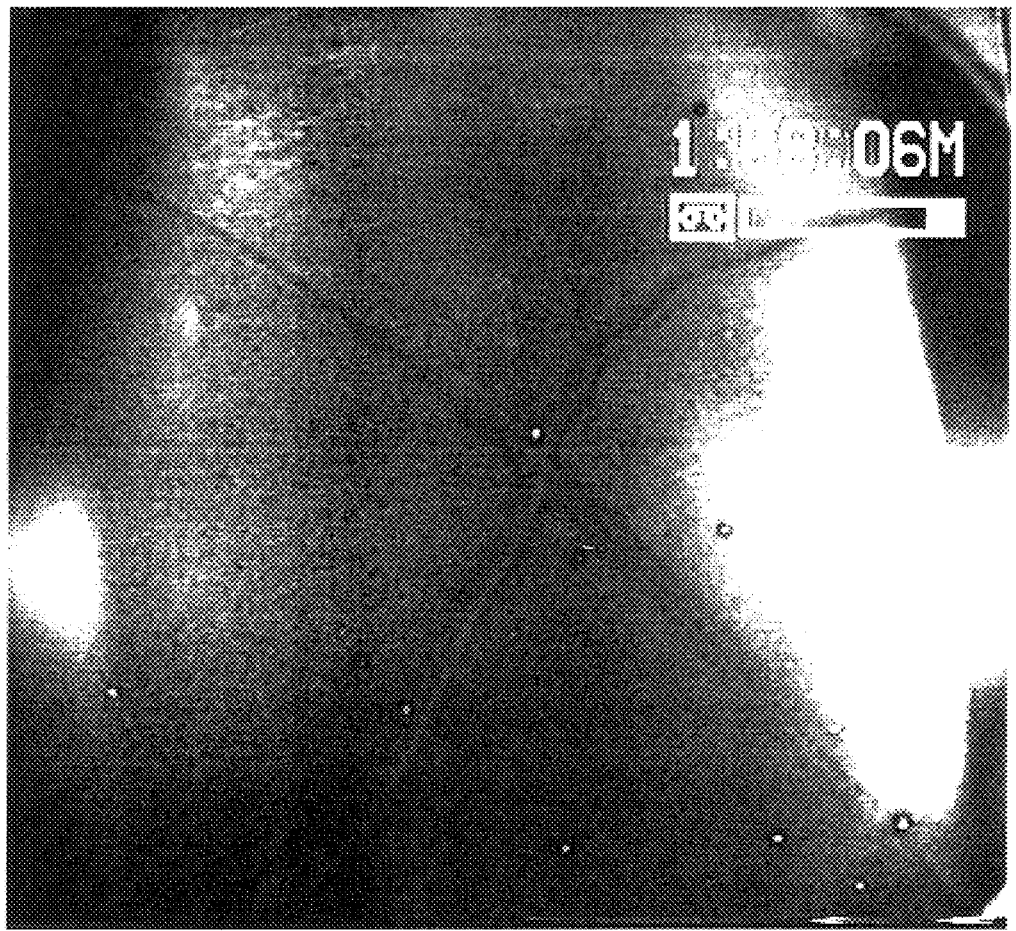
FIG. 12 is a photograph that illustrates the light scattering pattern of the condensate on a contaminated wafer with polystyrene latex particles of 55 nm and 100 nm deposited as two thin lines as detected by a camera.
Figure 13:
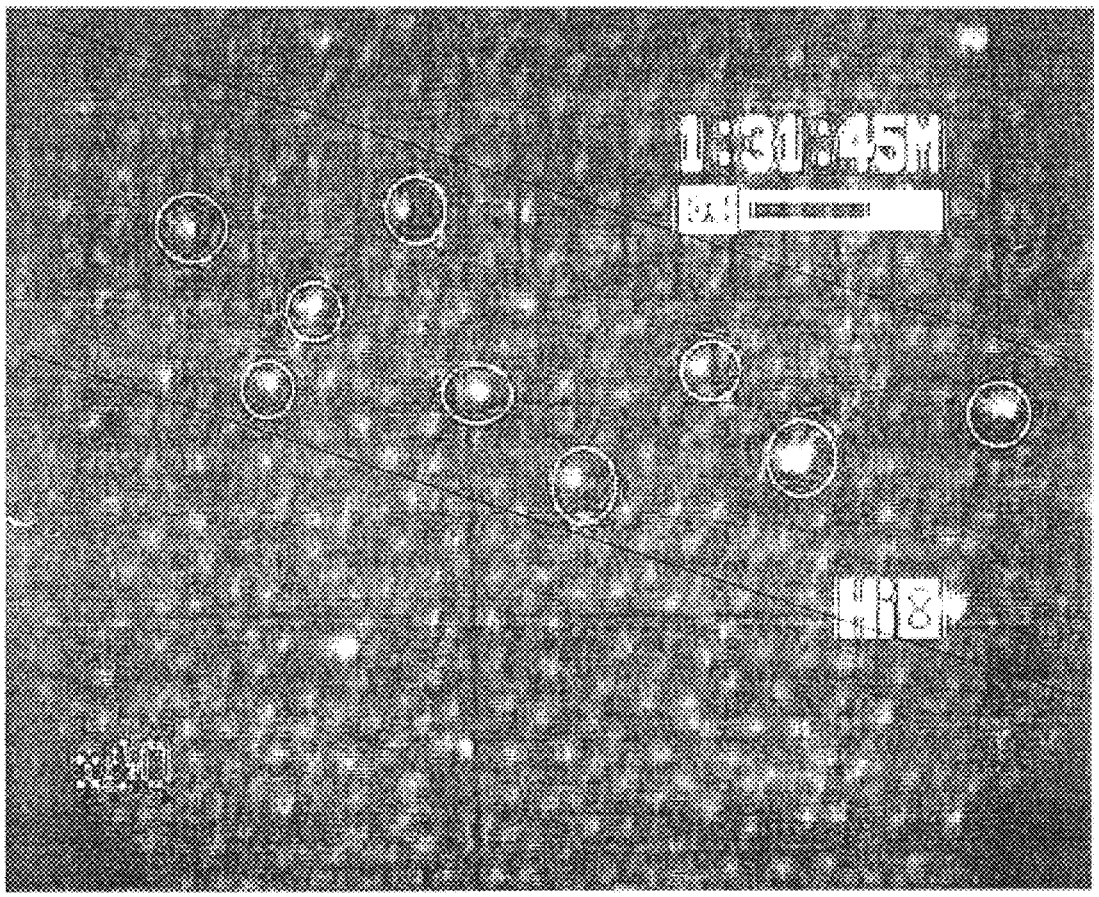
FIG. 13 is a photograph of a surface magnified (40×) by optical microscope and illustrates the light scattering pattern of the condensate on a seeded area of 55 nm polystyrene latex particles on a wafer.

FIG. 13 shows the detailed image, magnified 40 times, of the condensate on the seeded area of the wafer illustrated in FIG. 12. An optical microscope, Leica MG-3, was used to obtain the results of FIG. 13.

Figure 14:
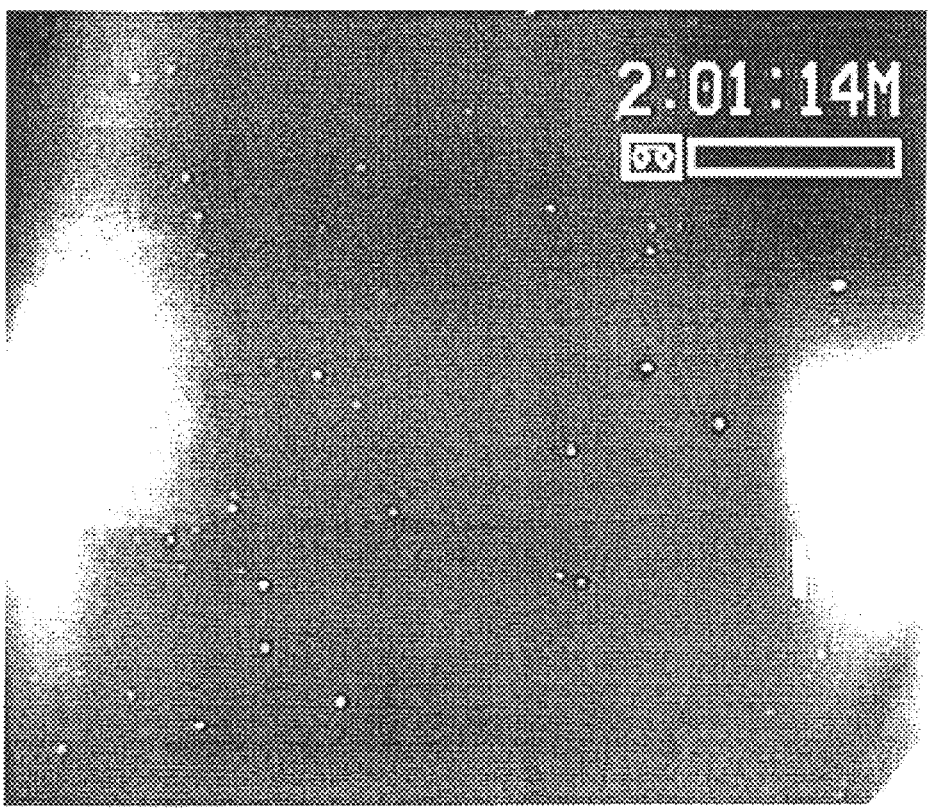
FIG. 14 is a photograph that illustrates the light scattering pattern of the condensate on a contaminated wafer having particles of 50 nm in diameter deposited as a wide centerline detected by high sensitivity video camera.

Polystyrene latex particles of 50 nm were deposited in the center of an undoped wafer in a wide line (wafer number 8 of Table I). The wafer was then subject to the method described above. The condensate results of the invention are shown in FIG. 14. The different light scattering pattern allows you to easily distinguish between the clear and seeded zone in the center of the photograph. This example demonstrates that the present invention is sensitive to particle contamination upon the surface of the test sample.

EXAMPLE 7

Figure 15A:
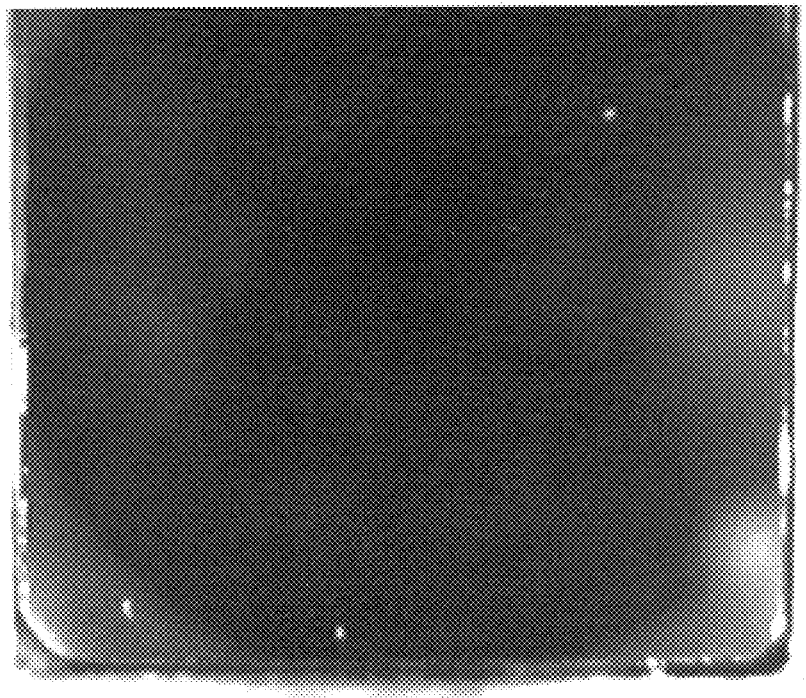
FIGS. 15A–15H are photographs that illustrate the light scattering pattern during the process as the water vapor content in the flow increases and then decreases over a wafer detected by a video camera.
Figure 15B:
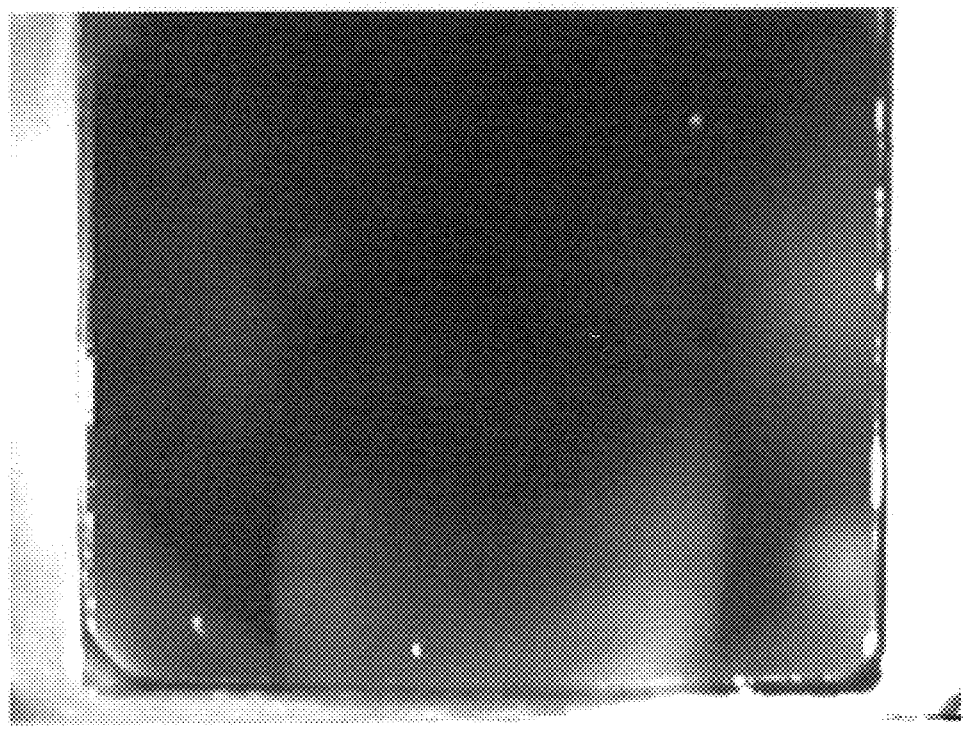
Figure 15C:
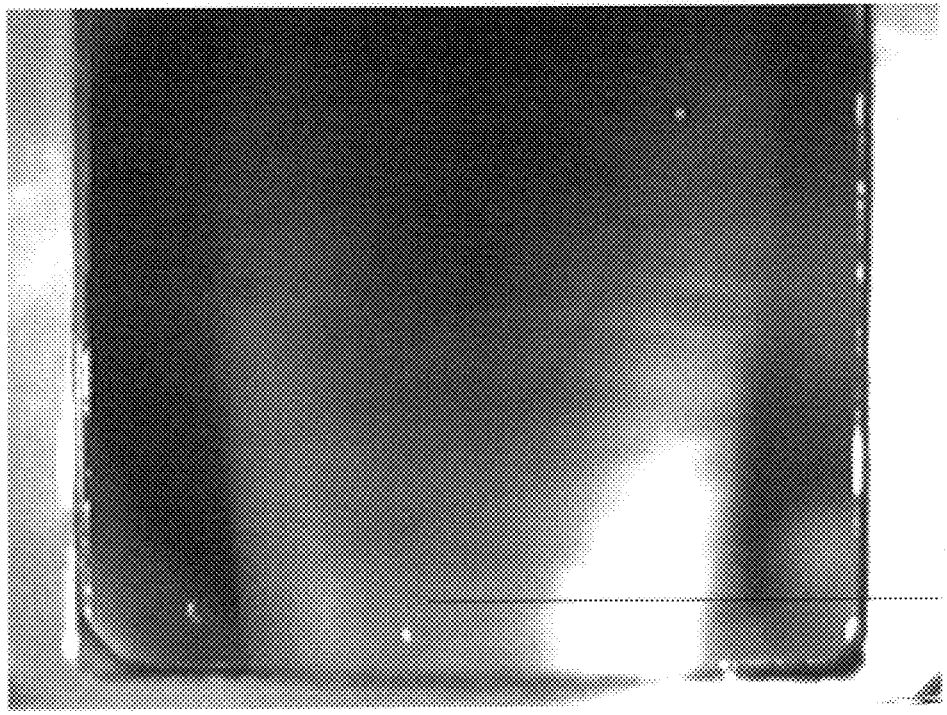
Figure 15D:
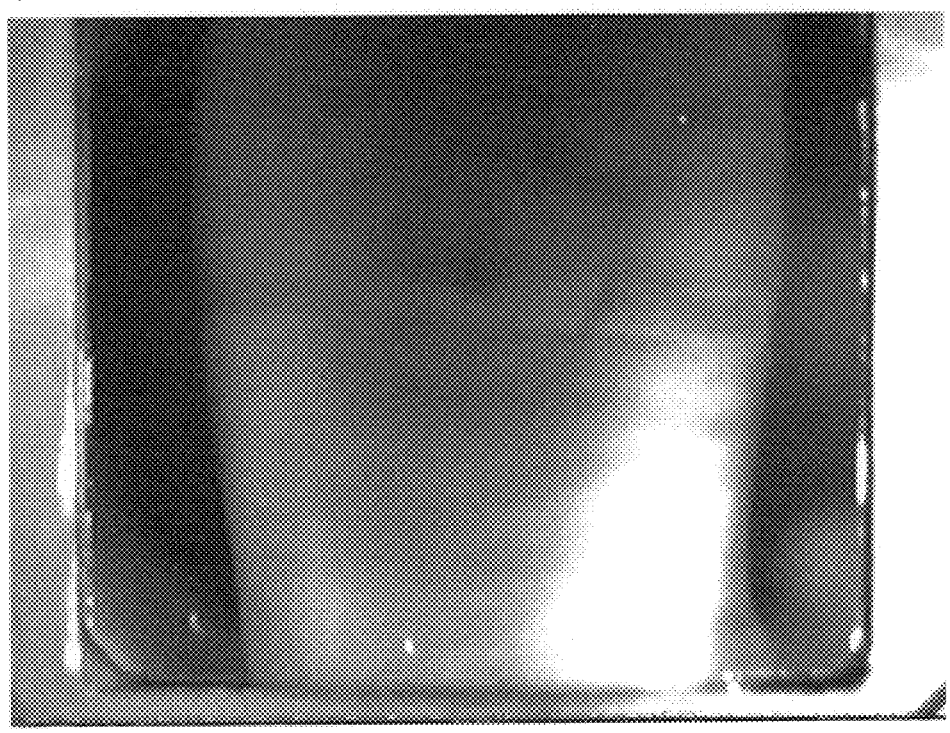
Figure 15E:
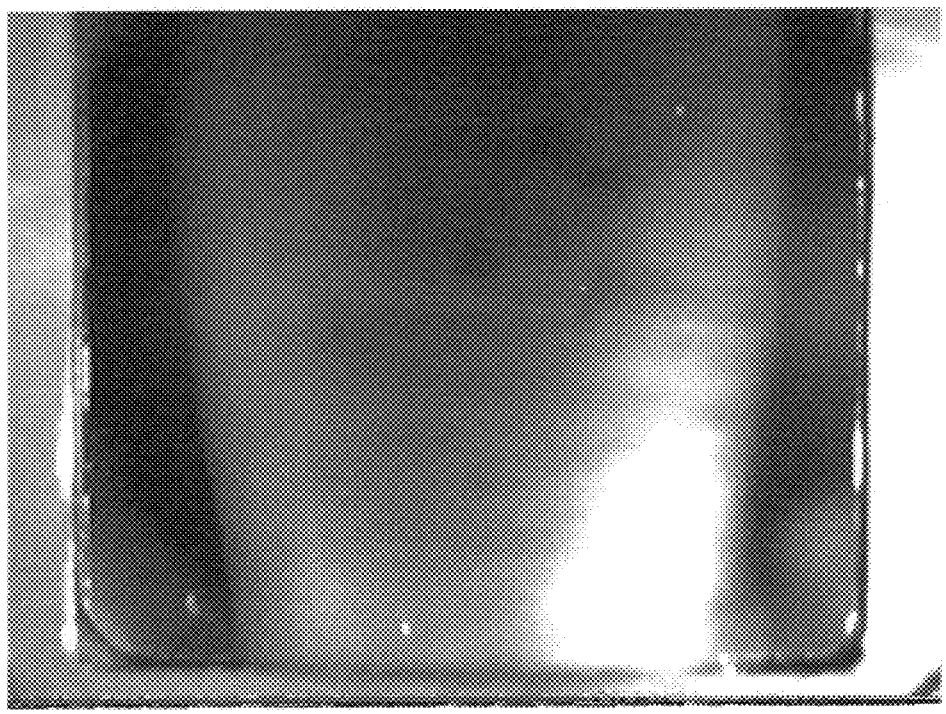
Figure 15F:
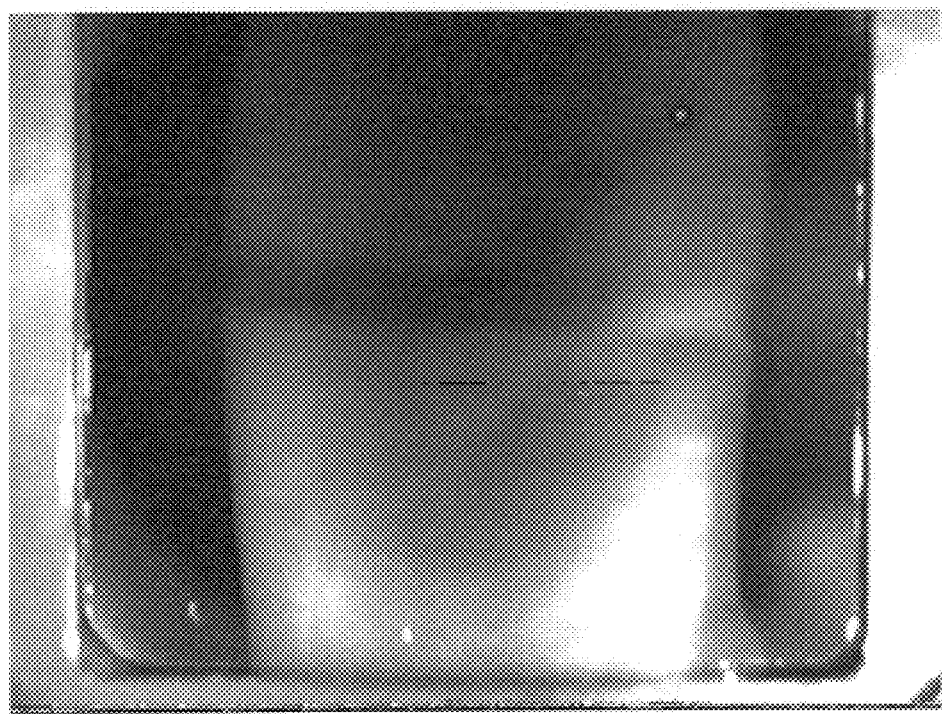
Figure 15G:
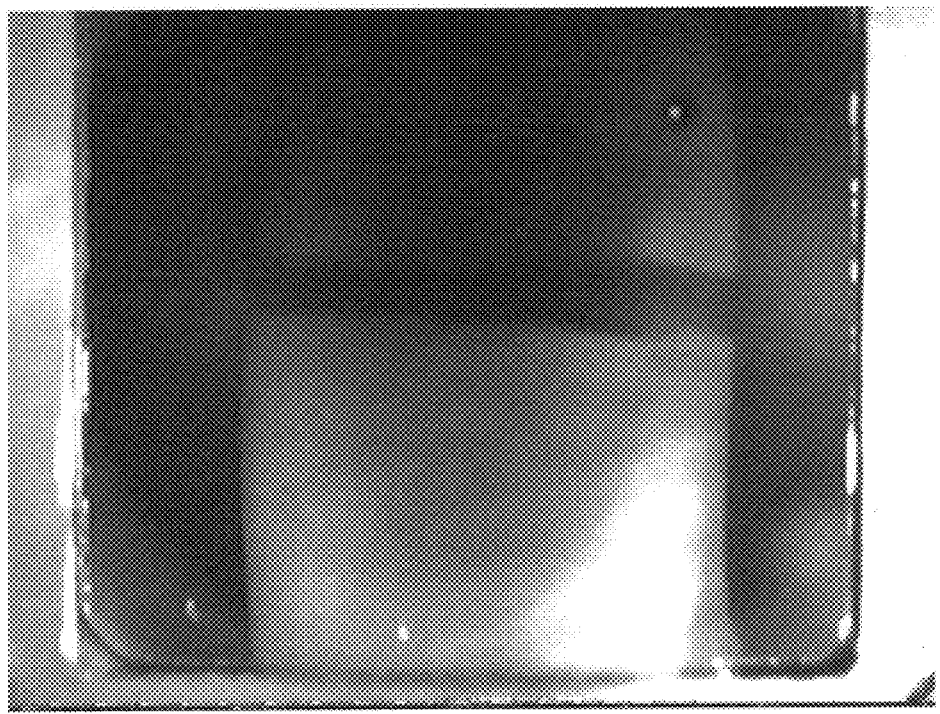
Figure 15H:
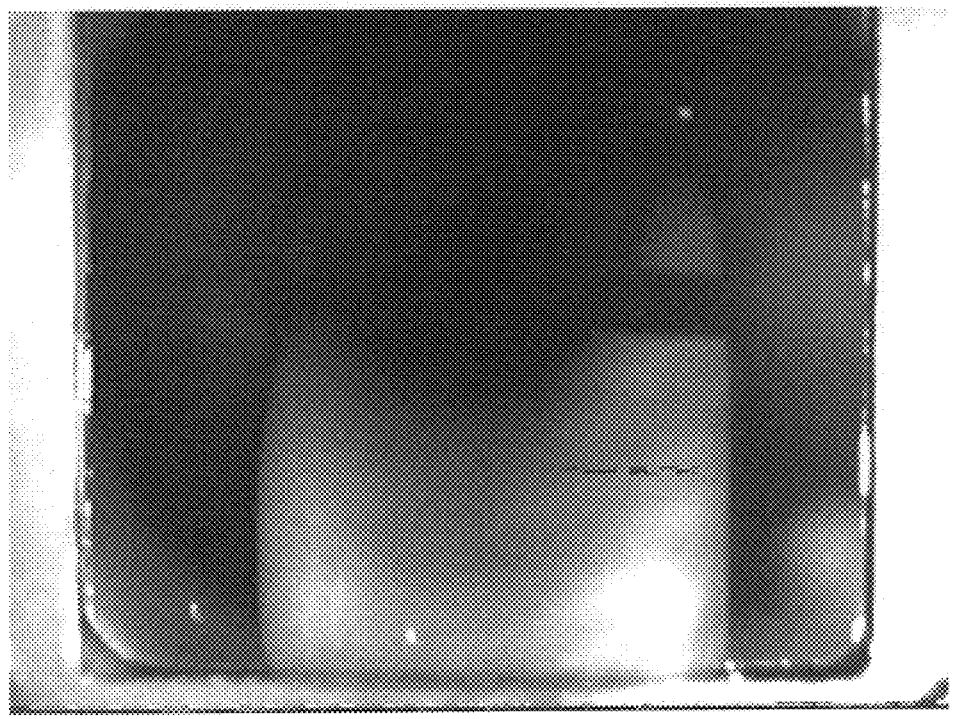

This example demonstrates that the present invention is very sensitive to particle contamination of the vapor surface. This example demonstrates the use of the invention to determine the enhanced detection of surface anomalies during condensation/evaporation dynamics. FIGS. 15A–H illustrate the process. FIG. 15A shows the beginning of the vapor delivery to the wafer (wafer number 3 of Table I). FIG. 15B shows the continuation of the vapor delivery. The start of condensation is evident at the bottom of the photograph. FIG. 15C shows the spread of condensation across the wafer as the vapor is still being delivered to the chamber holding the wafer. FIG. 15D shows the further continuation of the vapor delivery with the spread of condensation over the entire surface of the wafer. FIG. 15E shows the wafer as the vapor flow rate is stopped; dry nitrogen is still flowing over the vapor surface. FIG. 15F shows the shrinking of the condensation zone with the continued delivery of just the nitrogen gas. FIG. 15G shows the condensation zone further shrinking and the film deposited area becoming free of the condensate and clearly visible. FIG. 15H shows the disappearance of the condensate zone.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

What is claimed is:

1. A method of determining the characteristics of a surface of a sample comprising:
   (a) exposing the surface to a supersaturated vapor;
   (b) providing conditions causing the vapor to form droplets on the surface, the size, concentration and distribution of the droplets depending upon the characteristics of the surface;
   (c) illuminating the entire surface simultaneously;
   (d) detecting a pattern of scattered and reflected light from the droplets on the entire surface, during or after the formation of the droplets; and
   (e) determining the characteristics of the surface from the pattern so detected.

2. The method according to claim 1, wherein the surface is illuminated by a light source.

3. The method according to claim 2, wherein the light source is a white light.

4. The method according to claim 2, wherein the light source is a laser.

5. The method according to claim 1, wherein the scattered and reflected light is detected by a photo camera.

6. The method according to claim 1, wherein the scattered and reflected light is detected by a video camera.

7. The method according to claim 1, wherein the supersaturated vapor is nitrogen containing water vapor.

8. The method according to claim 1, wherein the vapor is caused to form droplets on the surface by maintaining the surface at a temperature cooler than the temperature of the vapor.

9. The method according to claim 8, wherein the surface is maintained cooler than the vapor by a thermoelectric cooler.

10. A method of determining the characteristics of a surface of a sample comprising:
    (a) exposing the surface of the sample to a supersaturated vapor;
    (b) illuminating the entire surface simultaneously;
    (c) providing conditions causing the vapor to form droplets on the surface, the size, concentration and distribution of the droplets depending upon the characteristics of the surface;
    (d) providing conditions causing the droplets to evaporate from the surface;
    (e) detecting a pattern of scattered and reflected light from the droplets during the evaporation of droplets from the surface; and
    (f) determining the characteristics of the surface from the pattern so detected.

11. A method according to claim 10, wherein the surface is illuminated by a light source.

12. A method according to claim 11, wherein the light source is a white light.

13. A method according to claim 11, wherein the light source is a laser.

14. A method according to claim 10, wherein the scattered and reflected light is detected by a photo camera.

15. A method according to claim 10, wherein the scattered and reflected light is detected by a video camera.

16. A method according to claim 10, wherein the supersaturated vapor is nitrogen containing water vapor.

17. The method according to claim 10, wherein the vapor is caused to form droplets on the surface by maintaining the surface at a temperature cooler than the temperature of the vapor.

18. A method according to claim 17, wherein the surface is maintained cooler than the vapor by a thermoelectric cooler.

19. A method according to claim 10, wherein the reflected and scattered light is also detected during condensation.

20. A method according to claim 19, wherein the characteristics of the surface are determined from changes occurring in the pattern of scattered and reflected light from the droplets during condensation and evaporation.

21. An apparatus for determining the characteristics of a surface of a sample comprising:
    (a) a test chamber adapted to receive a vaporizable material, the test chamber having an optical inlet and an optical outlet, and further having an inlet conduit and an outlet conduit;
    (b) a holder for the sample;
    (c) a cooler operatively connected to the test chamber;
    (d) a source of vaporizable material connected to the inlet conduit;
    (e) a light source adapted to transmit light onto the entire surface of the sample simultaneously through the optical inlet; and (f) a detector adapted to receive light scattered or reflected from the entire surface through the optical outlet.

22. An apparatus according to claim 21, wherein the light source is a white light.

23. An apparatus according to claim 21, wherein the light source is a laser.

24. An apparatus according to claim 21, wherein the cooler is a thermoelectric cooler.

25. An apparatus according to claim 21, wherein the detector is a photo camera.

26. An apparatus according to claim 21, wherein the detector is a video camera.

27. An apparatus according to claim 21, wherein the vaporizable material is nitrogen containing water vapor.

\* \* \* \* \*